United States Patent [19]

Kee et al.

[11] Patent Number: 5,333,607
[45] Date of Patent: Aug. 2, 1994

[54] VENTILATOR MANIFOLD WITH ACCESSORY ACCESS PORT

[75] Inventors: Kok-Hiong Kee; James G. Schneider, both of St. Louis, Mo.; Robert H. Bruno, Avon, Conn.

[73] Assignee: Sherwood Medical Company, St. Louis, Mo.

[21] Appl. No.: 962,755

[22] Filed: Oct. 19, 1992

[51] Int. Cl.$^5$ ............................................. A61M 16/00
[52] U.S. Cl. ..................... 128/204.18; 128/207.14; 128/912; 128/202.27; 128/207.16; 604/171; 604/167
[58] Field of Search ............... 128/911, 912, 204.18, 128/200.23, 202.27, 203.12, 200.22, 205.13, 207.14, 207.16, DIG. 26; 604/171, 172, 247, 167, 169; 285/331, 332, 330, 332.1

[56] References Cited

U.S. PATENT DOCUMENTS

| | | | |
|---|---|---|---|
| 1,588,336 | 6/1926 | Richmond | 285/331 X |
| 3,416,567 | 12/1968 | Von Dardel et al. | 137/604 |
| 4,240,417 | 12/1980 | Holever | 128/203.12 |
| 4,346,702 | 8/1982 | Kubota | 128/207.14 |
| 4,351,328 | 9/1982 | Bodai | 128/202.16 |
| 4,426,062 | 1/1984 | Bowron | 251/7 |
| 4,510,933 | 4/1985 | Wendt | 128/207.14 |
| 4,569,344 | 2/1986 | Palmer | 128/207.16 |
| 4,781,702 | 11/1988 | Herrli | 604/244 |
| 4,805,611 | 2/1989 | Hodgkins | 128/207.14 |
| 4,836,199 | 6/1989 | Palmer | 128/207.16 |
| 4,850,350 | 7/1989 | Jackson | 128/207.16 |
| 4,857,062 | 8/1989 | Russell | 604/256 |
| 4,951,661 | 8/1990 | Sladek | 128/202.27 |
| 5,009,391 | 4/1991 | Steigerwald | 251/149.1 |
| 5,083,561 | 1/1992 | Russo | 128/207.16 |
| 5,158,569 | 10/1992 | Strickland | 604/283 |
| 5,215,522 | 6/1993 | Page et al. | 604/33 |

Primary Examiner—Edgar S. Burr
Assistant Examiner—Eric P. Raciti
Attorney, Agent, or Firm—Andrew J. Beck; Montgomery W. Smith; Gene B. Kartchner

[57] ABSTRACT

A ventilator manifold is disclosed which includes a port for attachment and detachment of an accessory device thereto without interruption of continuous respiratory support of the patient. A particular embodiment of an accessory device described herein includes a suctioning device for removal of fluids from a patient's lungs during respiratory support. The manifold includes an accessory access port which has a normally closed valve therein which remains closed regardless of the pressure changes within the manifold. The normally closed valve is positioned in the port such that placement of a specially designed adaptor therein located on the suctioning device forces the normally closed valve to an open position, thus allowing passage of a suction catheter through the manifold into the patient. Removal of the adaptor of the suctioning device allows the normally closed valve to return to its closed position, thus allowing continued operation of the respiratory system even when no accessory device is present in the accessory device access port. The adaptor includes a housing which is specially adapted to be securable within the valve in the access port of the manifold so as to substantially inhibit pressure loss from the manifold while simultaneously forcing the valve to an open position. The manifold and valve are adapted to allow cleaning and lavage therethrough without detachment thereof.

17 Claims, 2 Drawing Sheets

VENTILATOR MANIFOLD WITH ACCESSORY ACCESS PORT

BACKGROUND OF THE INVENTION

1. Field of the Invention

This invention relates generally to apparatus used in conjunction with respiratory support systems. More specifically, the present invention relates to a method and apparatus for the attachment of accessory devices to a respiratory support system. Even more specifically, the present invention relates to a ventilator manifold of a respiratory system which accommodates the attachment and detachment of accessory devices therewith without interrupting or inhibiting the continuous respiration assistance being given to a patient by the respiratory system.

2. Prior Art

Respiratory systems used for the ventilation of critically ill patients are now commonly used in medical facilities. Typically, a prior art respiratory system includes a tracheal tube, positioned either directly, or through the nose or mouth, into the trachea of a patient, a manifold connected to the tracheal tube at one port position thereof, and a source of breathable gas connected at a second port thereof. The purpose of the respiratory system is to assist the patient in maintaining adequate blood oxygenation levels without over taxation of the patient's heart or lungs.

While a patient is attached to a respiratory system, it is periodically necessary to remove fluid from the patient's trachea or lungs. In the past, it has been necessary to disassemble part of the respiratory system, either by removing the manifold, or by opening a port thereof, and inserting a small diameter suction tube down the tracheal tube and into the patient's trachea and lungs. The fluid was then suctioned from the patient and the suction catheter was removed and the respiratory system reassembled. Due to the resulting interruption in respiratory support, a patient's blood oxygen often dropped to an unacceptably low level during the suctioning procedure, even when other previously known breathing assisting efforts were simultaneously provided.

One solution to the above problem, which is generally exemplary of the prior art, is shown in U.S. Pat. No. 5,073,164 by Hollister et al. in which the ventilator manifold includes a port thereon which is adapted to receive a connector of the suctioning device. The suctioning device positions a suction catheter within the manifold without substantial manifold pressure loss. The suction device includes an envelope which is positioned around the suction catheter in order to prevent contamination of the suction catheter surface which is intended to be inserted into the patient's trachea and lungs. Although this type of ventilator manifold and suctioning device connection allows continuous respiratory support of the patient during suctioning of fluid from the patient's trachea and lungs, there nevertheless remain several drawbacks associated with its use. For example, removal of the suctioning device from the manifold, such as for the purpose of replacing the suctioning device or attaching another accessory to the manifold, e.g. a manual resuscitation bag or a metered dose inhaler, cannot be accomplished without loosing manifold pressure and compromising the integrity of the respiratory system. Thus, respiratory support of the patient must be stopped whenever the suctioning device is removed from the manifold.

U.S. Pat. No. 4,351,328 to Bodai attempts to solve this problem by forming an opening in the ventilator manifold which is blocked by a pre-punctured resilient seal through which a suction catheter can be passed without substantially affecting the integrity of the system, i.e., without substantial gas exchange or pressure loss between the interior of the manifold and the atmosphere. The Bodai device, although allowing entry and removal of a suction catheter through a ventilator manifold during continuous respirator support of a patient, nevertheless fails to completely resolve the existing problem in the prior art. Specifically, the pre-punctured resilient material in the port allows only for the insertion of a suction catheter therethrough, and fails to accommodate a suctioning device which include a collapsible envelope for surrounding and protecting the catheter against contamination of its exterior surface. Further, there is no design consideration for the attachment of other accessory devices, such as a manual resuscitation bag or a metered dose inhaler, which are often necessary for use in the care of a patient.

Also, the system described by Bodai tends to cause mucous and other fluids from the patient's lungs and trachea to collect in the manifold as it is wiped from the prepunctured resilient seal when the suction catheter is removed therefrom. Because of this design problem, it is often necessary to replace the manifold of the respiration system more frequently than would otherwise be desirable.

There therefore exists a need in the art for a respiratory system which includes a ventilator manifold which allows simple attachment and detachment of accessory devices during continuous patient respiratory support without substantial pressure loss from the system and without substantial collection of body fluids in the manifold. And a respiratory manifold which can be easily clean of mucus and other fluids which may collect therein during use without the necessity of removing the accessory device therefrom.

OBJECTS AND SUMMARY OF THE INVENTION

A principle object of the present invention is to provide a patient respiratory system which allows access thereto of accessory devices, such as a suction catheter device, without interruption of continuous patient respiratory support.

Another object of the present invention is to provide a respiratory system which allows access of accessory devices thereto through an accessory access port within the manifold which is normally closed against the atmosphere and which will open upon attachment of the accessory device and automatically reclose upon detachment thereof.

A further object of the present invention is to provide a respiratory system having a manifold which includes an accessory device access port with a normally closed valve therein, which can accommodate an adaptor formed as part of the accessory device and designed to seal against the port and open, the normally closed valve allowing interchangeable use of accessory devices within the manifold while maintaining manifold pressure integrity.

Another object of the present invention is to provide a manifold for a respiratory system which includes an accessory device access port which is adapted to allow cleaning fluid to be injected therein in order to clean the adaptor and accessory device while positioned within the access port.

These and other objects of the present invention are realized in a presently preferred embodiment thereof, described by way of example and not necessarily by way of limitation, which provides for interchangeable use of accessory devices with a manifold of a respiratory system during respiratory support of a patient, without comprising the integrity of the system by causing significant pressure loss through the manifold. The invention includes a ventilator manifold formed with an accessory device access port which includes a normally closed valve therein. The valve maintains the pressure differential between the atmosphere and the interior of the manifold regardless of manifold pressure fluctuations. The accessory device access port also includes a sleeve member positioned within the port, so as to line the port interior surface, which assists in sealing against an adaptor inserted into the port. The sleeve member also passes through a side opening in the port and attaches to a pigtail type fluid injection tube which is adapted for allowing injection of fluid therethrough into the access port and through the sleeve member into the adaptor. The pigtail may also include a one-way valve therein for preventing retrograde movement of fluid therethrough.

The invention may also include the adaptor which is formed to fit within the accessory device access port and sealingly engage with the sleeve member and the normally closed valve. Positioning the adaptor into the access port forces the normally closed valve to an open position. The access port and adaptor include a detent and stop-type locking arrangement for locking the adaptor within the port against inadvertent withdraw thereof during use, and for properly orienting the adaptor within the port to form a clear passage through the port and adaptor for the insertion and removal of a medical instrument. The adaptor includes a side opening therein which is orientable relative to the stop-type locking mechanism on the adaptor to cause it to align with the side opening of the sleeve member and the access port when the adaptor is properly position within the access port and locked in place for use. The adaptor locking mechanism and the access port are designed to ensure that the adaptor can be inserted and locked into the access port in only one unique orientation therewith so as to ensure that the side opening of the adaptor is in alignment with the side opening of the sleeve member and the access port. In this manner, cleaning fluid may be injected through the fluid injection tube directly to the interior of the adaptor whenever the adaptor is properly locked in position within the access port. Any medical instrument or portion thereof located within the adaptor therefore can be easily cleaned without the necessity of removing the adaptor from the access port.

The adaptor may be formed as part of, or for use with, any one of a number of common respiratory system accessories, such as a suction catheter device, a metered dose inhaler, a manual resuscitation bag, a bronchoscope or the like.

In the presently shown preferred embodiment of the invention, the adaptor is part of a suction catheter device, and may include a seal through which the suction catheter thereof is inserted for extension through the manifold into the patient's trachea and lungs. The adaptor seal is designed to ensure that the internal pressure in the manifold is not lost through the adaptor, and that the cleaning fluid injected through the pigtail tube, which passes through the access port into the adaptor, will be effective in cleaning the suction catheter and will be entirely removed from within the manifold and the adaptor interior by suctioning through the suction catheter after it has performed its desired cleaning function and will not be allowed to accumulate within the adaptor or manifold, or to pass down the patient's trachea if not desired.

If desired, the manifold of the present invention may include swivel connectors at the patient attachment port and the ventilator circuit connection port thereof to allow rotation of the manifold relative to the trachea tube and/or the flexible breathing hoses from the respiratory system in order to increase the patient's comfort during use.

These and other objects and advantages of the present invention will become apparent from the following more detailed description, when taken in conjunction with the accompany drawings, in which like elements are identified with like numerals throughout.

DETAILED DESCRIPTION OF THE PREFERRED EMBODIMENTS

Figure 1:
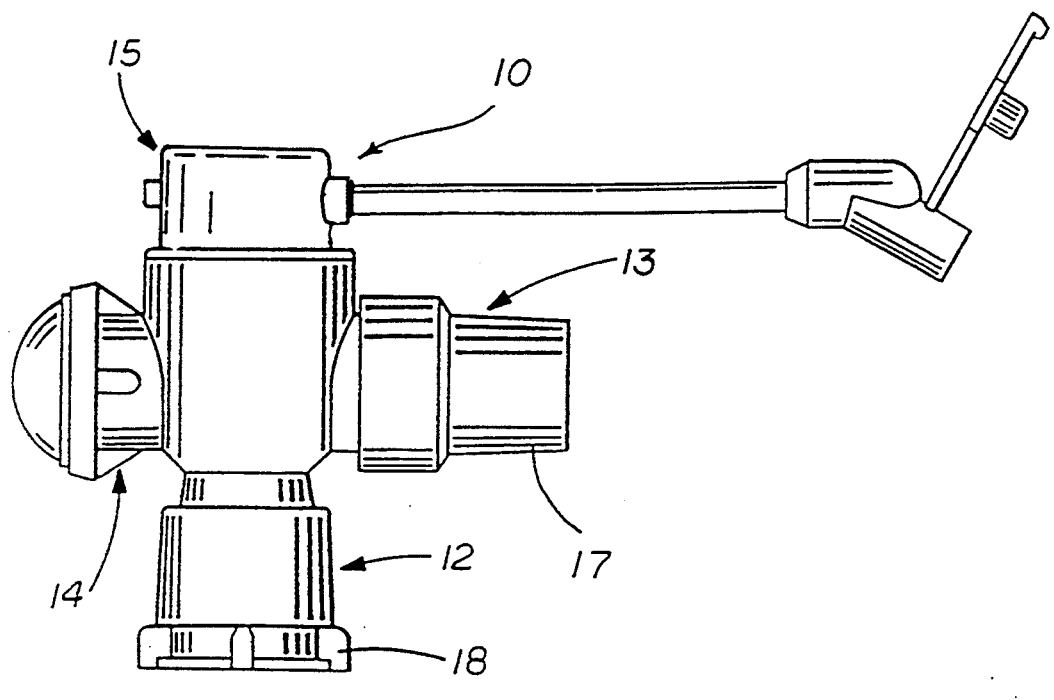
FIG. 1 shows a manifold of a respiratory support system which has been modified to include an accessory device access port formed in accordance with the principles of the present invention.

As shown in the exemplary drawings for the purposes of illustration, an embodiment of a ventilator manifold made in accordance with the principles of the present invention, referred to generally by the reference numeral 10, is provided for interchangeable access of respiratory system accessory devices. Also shown for purposes of illustration is an embodiment of an adaptor 11, formed as part of a suction catheter device, which is provided for air-tight attachment to the manifold 10. The respiratory system and accessory devices therefore are more completely described in applicant's copending U.S. patent application Ser. No. 07/962,756 filed Oct. 19, 1992, incorporated herein in its entirety by reference.

As shown in FIG. 1, the ventilator manifold 10 of the present invention includes a plurality of access ports which facilitate its connection to a patient and to a ventilator circuit of the respiratory system. The manifold 10 is attached to a patient for fluid flow communication with the patient's lungs by the connection of the patient attachment port 12 thereof to the connector of an endotracheal tube assembly (not shown) which has been previously positioned in the trachea of a patient by any one of several well known procedures.

The weaning port 14 is normally kept covered by a cap (not shown), and the ventilator circuit connection port 13 of the manifold 10 is connected to flexible breathing hoses from the respiratory system (also not shown) in a well known manner, such as through a "Y" site connector.

The ventilator circuit connection port 13 and the patient attachment port 12 may, if desired, include swivel connectors 17 and 18 respectively thereon in order to allow relative rotation between the manifold 10 and the trachea tube and breathing hoses in order to isolate the trachea tube from the incidental forces causes by the manifold 10 or the breathing hoses attached thereto so as to increase the comfort of the patient.

The ventilator circuit attached to port 13 provides a high oxygen content gas mixture to the patient and receives the expelled air from the patient. The ventilator circuit commonly includes various valves, regulators and the like associated with the hoses attached to the port 13 to effect respiration of the patient. The manifold 10, and hoses attached thereto at the ventilator circuit connection port 13, are generally made of disposable plastic material and are intended to be used by only one patient and then discarded.

When attached to the patient, the entire respiratory system is designed to isolate the patient's lungs from the atmosphere and allow pressurized forced ventilation of a gas mixture of a high oxygen content from the ventilator into the patient's lungs. Commonly, respiratory systems of this type are used to maintain a positive end expiratory pressure (PEEP) within the ventilator manifold 10 and the patient's lungs at all times during exhalation. This technique is used because of its benefit of ensuring that a minimum concentration of oxygen is supplied to the patient to maintain proper blood oxygenation levels. The PEEP procedure keeps a large number of lung alveoli of the patient open at all times during respiratory support, thus increasing the effective lung area subject to ventilation.

Prevailing respiratory support techniques, including PEEP, have made it very disadvantageous to interrupt respiratory support of the patient by opening the respiratory system manifold 10 to the atmosphere, (or by detaching hoses from the ventilator circuit connection port 13). Therefore, the repeated attachment and detachment of accessory devices such as a suction catheter device or the like for necessary medical procedures has had to be avoided because of the loss of isolation of the respiratory system from the atmosphere during these procedures, and the immediate loss of effective lung surface area due to alveoli collapse. Further, when such procedures take an extended period of time to perform, blood oxygen can drop to inadequate levels, and cause the patient to over exert the lungs and heart when trying to return the blood oxygenation level to normal. Also, disassembly and reassembly of the respiratory system for procedures with prior art accessory devices has in the past been very time consuming for the medical worker.

The present invention resolves the problems associated with loss of isolation of the respiratory system from the atmosphere (i.e. loss of PEEP) when these various accessory devices must be attached or detached for use in performing necessary medical procedures during respiratory support. Specifically, the manifold 10 of the present invention includes an accessory device access port 15 which is in fluid flow communication with the interior of the manifold 10 and the atmosphere and which can be accessed without loss of PEEP.

Figure 2:
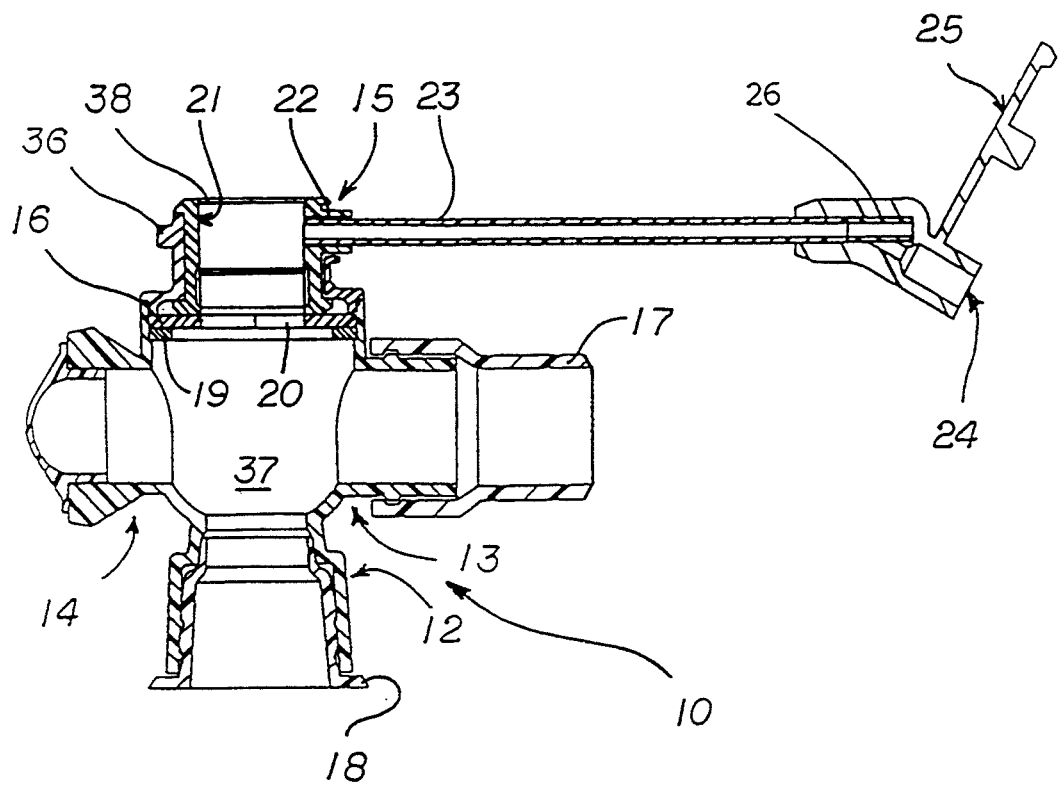
FIG. 2 shows a cross-sectional view of the ventilator manifold.

As best shown in FIG. 2, the access port 15 includes a normally closed valve 16 formed therein which maintains the interior of the manifold 10 isolated from the atmosphere at all times. As explained above, the interior of the manifold 10, although experiencing constant pressure fluctuations, is generally kept at a pressure which is slightly above atmospheric pressure in order to properly administer oxygen according to the PEEP procedure. Therefore, the valve 16 is preferably made of a resilient material to ensure that pressure isolation of the manifold 10 is maintained.

Figure 4:
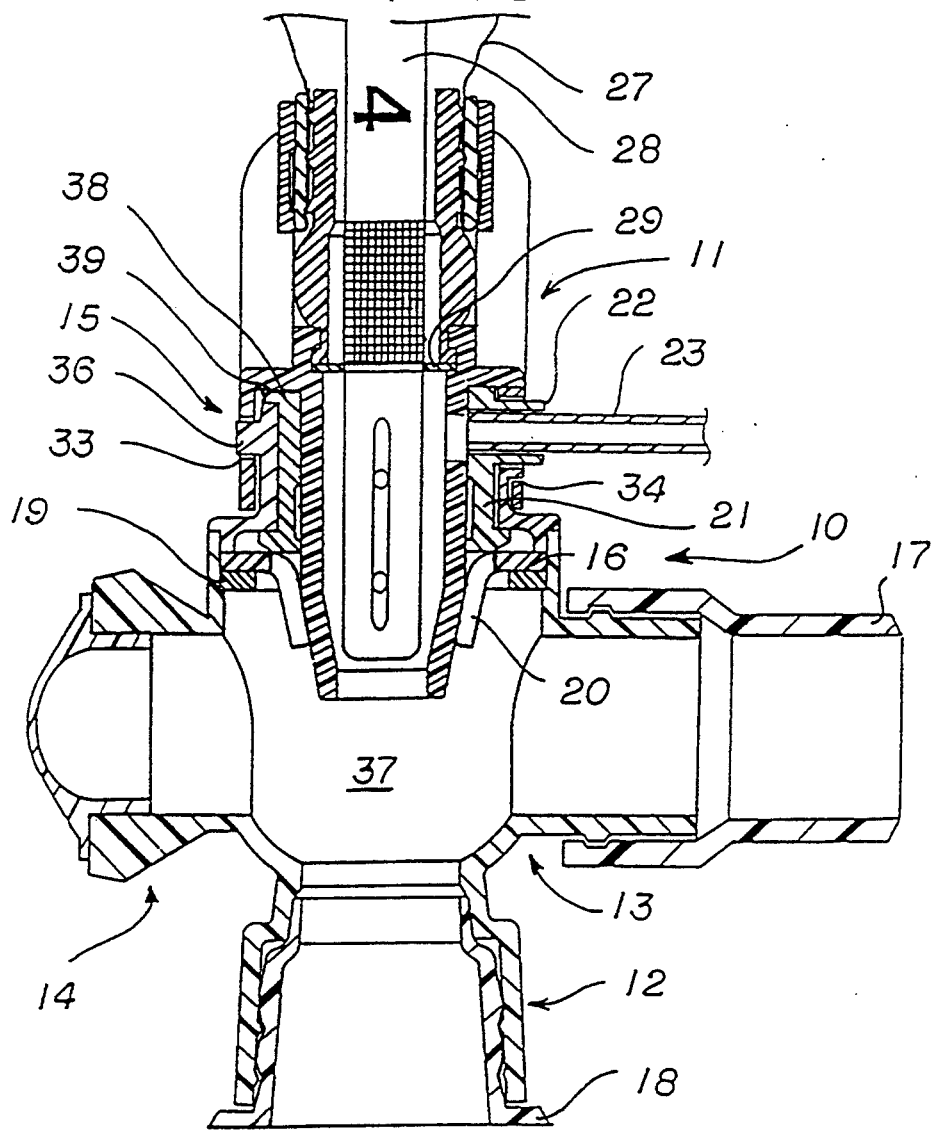
FIG. 4 is a cross-sectional view of the manifold with the adaptor attached thereto.

The valve 16 is preferably formed to a circular disk shape and inserted into the manifold 10 between the access port 15 and a support ring 19. The valve 16 is formed with a slit, or a pair of perpendicular slits 20 which are normally closed against fluid flow therethrough, but may be forced opened by the insertion of the adaptor 11 therethrough (as shown in FIG. 4).

The interior of the access port 15 is lined with a sleeve member 21 which covers the entire interior surface of the access port 15 and abuts in sealing relationship against the normally closed valve 16. The interior diameter of the sleeve member 21 is predetermined to cause a snug fit with the adaptor 11 (as best shown in FIG. 4) to assist in the prevention of leakage from the manifold 10 when the normally closed valve 16 is forced opened by the adaptor 11.

The access port 15 forms a side opening 22 therethrough through which a portion of the sleeve 21 extends to be attached, such as by solvent bonding, to a pigtail fluid injection tube 23 which is intended for use in transporting fluid through the access port side opening 22 into the interior of the access port 15. The opposite end of the pigtail tube 23 includes a luer connector 24 attached thereto with an integrally formed luer connector plug 25. A check valve 26, taking the form of a collapsible sleeve, is positioned between the luer connector 24 and the pigtail tube 23 and collapses upon injection of fluid through the luer connector 24 into the pigtail tube 23, but expands to block fluid flow in the opposite direction.

It is preferred that the sleeve member 21 be formed of a relatively flexible material such as plasticized PVC, having good solvent bonding characteristics with the material forming the pigtail tube 23, the pigtail tube 23 preferably being formed of the same material as the sleeve member 21. The access port 15 according to the preferred embodiment of the present invention is preferably formed of clear ABS, which is preferably the same material forming the main body of the manifold 10 in order to ensure good ultrasonic or solvent bonding therebetween.

Figure 3:
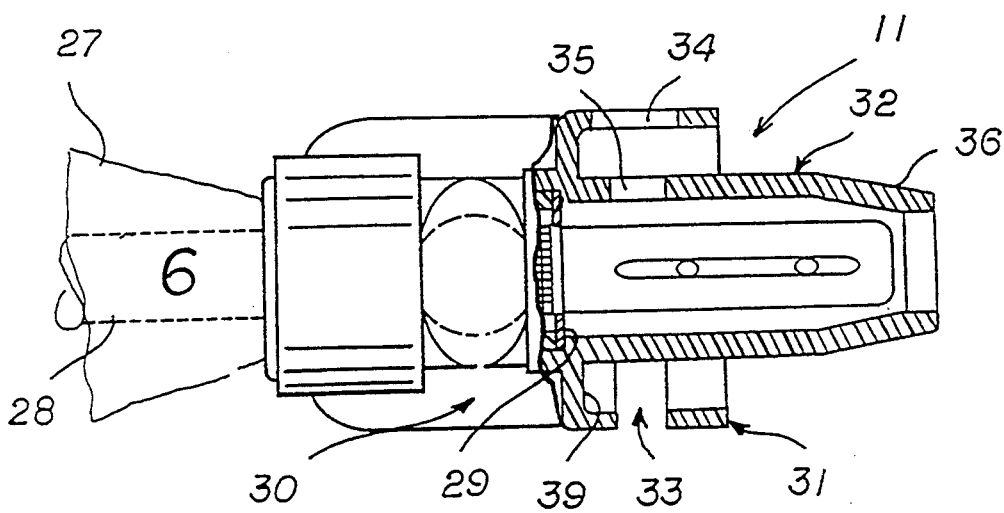
FIG. 3 is a partial cutaway view of a portion of an accessory device which includes an adaptor formed in accordance with the principles of the present invention.

In FIG. 3, a partial cross-sectional view of the adaptor 11 of the present invention as attached to an accessory device is shown. The accessory device (shown only in part) in the preferred embodiment of the invention is a suction catheter device. Many important aspects of the adaptor 11 of the present invention are disclosed in applicant's copending U.S. application Ser. No. 07/962,756 filed Oct. 19, 1992, which is incorporated herein by reference in its entirety.

The adaptor 11 of the present invention is permanently attached to the distal end of a sheath 27 which is designed to isolate the suction catheter 28 from direct contact with the user. Further, in the present embodiment, the adaptor 11 preferably includes a sealing ring 29 formed in the housing 30 thereof through which the suction catheter 28 must pass in order to pass through the adaptor 11 and into the manifold 10 during use. The seal ring 29 is designed to allow movement of the suction catheter 28 therethrough while at the same time maintain a seal thereabout.

A locking cylinder 31 may be formed to encircle a portion of the adaptor insertion member 32 and includes a pair of arcuate slots 33 and 34 which operate together as a locking mechanism to ensure secure attachment of the adaptor 11 to the access port 15 of the manifold 10, and also ensures proper relative orientation therebetween to cause the insertion member opening 35 of the adaptor 11 to be positioned in alignment with the side opening 22 of the access port 15 when the adaptor 11 is properly locked in position therein for use (as best shown in FIG. 4).

As can be seen, the arcuate slot 33 is sized to be engageable with the nub 36 which is located directly opposite the side opening 22 on the access port 15. The arcuate slot 34 is larger in width than the arcuate slot 33 and therefore can accommodate the side opening 22 of the access port 15. As is readily evident, since the arcuate slots 33 and 34 are sized differently to accommodate the nub 36 and the side opening 22 respectively, of the access port 15, the adaptor 11 can only locked in position within the access port 15 in one unique relative orientation therewith in which the insertion member opening 35 and the side opening 22 are in alignment.

As best shown in FIG. 4, attachment of the adaptor 11 to the respiratory manifold 10 is effected by insertion of the adaptor 11 into the access port 15 until the tapered top section 36 of the insertion member 32 engages the valve 16 and forces it toward the interior of the manifold 10. Upon complete insertion of the adaptor 11 into the port 15, the valve 16 is completely open and the sleeve member 21 is sealingly engaged with the insertion member 32. Also, the sleeve shoulder 38 of the sleeve member 21 is forced to resiliently deform within the base 39 of the locking cylinder 31. This increases the air tight seal and assists in positively locking the adaptor 11 to the access port 15 by forcing the arcuate slots 33 and 34 against the nub 36 and side opening 22 respectively.

It is intended that during insertion of the adaptor 11 into the access port 15, the sealing relationship formed between the sleeve member 21 and the insertion member 32 commence prior to opening of the valve 16 by the tapered top section 36, in order to ensure isolation of the interior of the manifold 10 from the atmosphere during attachment of the accessory device. Once completely inserted within the port 15, the tapered top section 36 extends completely through the access port 15 and into the manifold central chamber 37.

As shown in FIG. 4, the pigtail tube 23 can be used to inject fluid into the adaptor 11 to clean the suction catheter 28 and the sealing ring 29 of mucal materials which may have accumulated therein due to repeated insertion and withdrawn of the catheter 28 from the patient's lungs during aspiration procedures. The cleaning fluid can then be aspirated through the catheter 28 to remove it from the interior of the adaptor 11 and the manifold 10.

Alternatively, if desired, fluid may be injected through the pigtail tube 23, into the adaptor insertion member 32 and through the central chamber 37 of the manifold 10, and through the patient connection port 12 into the trachea and lungs of the patient for purposes of lavage. The suction catheter 28 can then be inserted through the manifold 10 into the patient's trachea and the fluid can be aspirated along with any mucal materials dislodged by the lavage fluid.

It should be understood from the foregoing that, while a particular embodiment of the invention has been illustrated and described, various modifications can be made thereto for its adaption to various accessory devices which may be used in conjunction with a respiratory system which require access to a patient's lungs while maintaining isolation of the respiratory system from the atmosphere. It is to be understood that adaption of the present invention for use on any such accessory device is intended to be well within the spirit and scope of the present invention.

When it is desired to remove the accessory device from the manifold 10, it is only necessary to unlock the adaptor 11 from the slots 33 and 34 of the access port 15, and withdraw the adaptor 11 therefrom. Due to the resilient nature of the valve 16, upon withdrawal of the adaptor 11 it will return to its normally closed position without exposure of the interior of the manifold 10 to the atmosphere. In this manner, accessory devices may be attached and detached periodically to the manifold 10 without interruption of continuous respiratory support of a patient by the respiratory system and without loss of isolation of the respiratory system from the atmosphere.

Although a particular embodiment of the invention has been shown, it is not intended that the invention be limited thereby, instead, the scope of the present invention is intended to be limited only by the appended claims.

We claim:

1. A ventilator manifold adapted for use with a respiratory support system, including a respiratory system accessory device having an adaptor, said manifold comprising:
   a fluid flow connection port for fluid flow connection between a patient and a ventilator circuit, and
   an accessory access port for allowing attachment of the adaptor to said manifold, said accessory access port being normally closed against fluid flow therethrough into said manifold,
   a locking device for locking the adaptor to said accessory access port, said locking device including means to allow locking of said adaptor and said manifold in only a single relative orientation,
   wherein, the adaptor further provides means for opening the accessory access port in response to attachment of the adaptor to said accessory access port to allow fluid flow access between said manifold and the respiratory system accessory device.

2. A ventilator manifold according to claim 1 wherein said accessory access port includes a normally closed valve therein, whereby, said normally closed valve is closed to fluid flow through said accessory access port and is forced to an open position by the adaptor to allow fluid flow through said accessory access port when the adaptor is properly positioned within said accessory access port.

3. A ventilator manifold according to claim 1 wherein said accessory access port further includes an injection fluid inlet opening therein.

4. A ventilator manifold according to claim 1 wherein said injection fluid inlet opening includes a one-way check valve therein.

5. A ventilator manifold according to claim 4 wherein said one-way check valve includes a collapsible sleeve.

6. A ventilator manifold according to claim 1 wherein said accessory access port includes a relatively flexible sleeve formed therein.

7. A ventilator manifold according to claim 6 wherein said relatively flexible sleeve formed within said accessory access port also forms a part of said injection fluid inlet opening.

8. A ventilator manifold according to claim 7 wherein said injection fluid inlet opening further includes an elongate hollow tube having a first end thereof attached to said sleeve and a second end attached to a luer connector.

9. A ventilator manifold according to claim 8 wherein said injection fluid inlet opening further includes a one-way valve therein.

10. A ventilator manifold according to claim 9 wherein said one-way valve of said injection fluid inlet opening is a collapsible sleeve valve.

11. A respiratory support system comprising:
 a manifold adapted to be connected for fluid flow attachment between a patient and a ventilator circuit said manifold including an injection fluid inlet opening therein,
 an adaptor formed as part of a respiratory system accessory device said adaptor including an injection fluid opening therein, and
 said manifold including an accessory access port for allowing attachment of said adaptor to said manifold, said accessory access port being normally closed against fluid flow therethrough,
 a locking device for locking the adaptor to said accessory access port, said locking device including means to allow locking of said adaptor and said manifold in only a single relative orientation,
 wherein, said adaptor further provides means for opening said accessory access port in response to attachment of said adaptor to said accessory port to allow fluid flow access between said manifold and said respiratory system accessory device, and locking of said adaptor to said accessory access port with said locking device operates to align said injection fluid inlet opening of said manifold with said injection fluid opening of said adaptor.

12. A respiratory support system according to claim 1 wherein said accessory access port includes a normally closed valve therein, whereby, said normally closed valve is closed to fluid flow through said accessory access port, and is forced to an open position by said adaptor to allow fluid flow through said accessory access port when said adaptor is properly positioned within said accessory access port.

13. A respiratory support system according to claim 12 wherein said adaptor is formed of a generally hollow tubular member having a proximal end and a distal end, said proximal end being attachable to a respiration system accessory, and said distal end including an insertion member for opening said normally closed valve of said accessory access port.

14. A respiratory support system according to claim 13 wherein said insertion member for opening said normally closed valve maintains a seal between said adaptor and said accessory access port when said adaptor is attached to said manifold.

15. A respiratory support system according to claim 14 wherein said means for opening said normally closed valve includes a semiconically shaped portion located at said distal end of said adaptor.

16. A respiratory support system according to claim 11 wherein said adaptor further includes a seal through which at least a portion of the respiratory system accessory device can pass into the manifold when said adaptor is attached to said accessory access port.

17. A respiratory support system according to claim 16 wherein the respiratory system accessory device is a suction catheter device, and the portion of the respiratory system accessory device which can pass through said seal includes a portion of a suction catheter.

\* \* \* \* \*